United States Patent
Pullagurla et al.

(10) Patent No.: US 10,647,655 B2
(45) Date of Patent: May 12, 2020

(54) METHOD FOR THE SYNTHESIS OF PERMETHRIN

(71) Applicant: BIOPHORE INDIA PHARMACEUTICALS PVT. LTD., Hyderabad (IN)

(72) Inventors: Manik Reddy Pullagurla, Hyderabad (IN); Mecheril Valsan Nanda Kumar, Hyderabad (IN); Madhusudhana Rao Veligetla, Hyderabad (IN); Jagadeesh Babu Rangisetty, Hyderabad (IN)

(73) Assignee: BIOPHORE INDIA PHARMACEUTICALS PVT. LTD. (IN)

( * ) Notice: Subject to any disclaimer, the term of this patent is extended or adjusted under 35 U.S.C. 154(b) by 0 days.

(21) Appl. No.: 16/329,770

(22) PCT Filed: Sep. 1, 2017

(86) PCT No.: PCT/IN2017/050377
§ 371 (c)(1),
(2) Date: Mar. 1, 2019

(87) PCT Pub. No.: WO2018/042461
PCT Pub. Date: Mar. 8, 2018

(65) Prior Publication Data
US 2019/0194118 A1    Jun. 27, 2019

(30) Foreign Application Priority Data

Sep. 2, 2016  (IN) .............................. 201641030143

(51) Int. Cl.
C07C 67/14 (2006.01)
C07C 67/52 (2006.01)
A01N 53/00 (2006.01)

(52) U.S. Cl.
CPC .............. *C07C 67/14* (2013.01); *A01N 53/00* (2013.01); *C07C 67/52* (2013.01); *C07B 2200/09* (2013.01); *C07C 2601/02* (2017.05)

(58) Field of Classification Search
None
See application file for complete search history.

(56) References Cited

U.S. PATENT DOCUMENTS 4,024,163 A  * 5/1977  Elliott .................... C07C 45/29
                                                        514/461
4,113,968 A    9/1978  Mori et al.

FOREIGN PATENT DOCUMENTS

IN                253251 A1     7/2012

OTHER PUBLICATIONS

Written Opinion of the International Searching Authortty—PCT/IN2017/050377 (Year: 2017).*
International Search Report; PCT/IN2017/050377; International Filing Date: Sep. 1, 2017.
Written Opinion; PCT/IN2017/050377; International Filing Date: Sep. 1, 2017.

* cited by examiner

*Primary Examiner* — Clinton A Brooks
*Assistant Examiner* — Kofi Adzamli
(74) *Attorney, Agent, or Firm* — Schmeiser, Olsen & Watts, LLP

(57) ABSTRACT

An improved method for the synthesis of substantially pure Permethrin having purity greater than 99.5% by Gas Chromatography provided. The embodiments also relates to a purification process of Permethrin by recrystallization from methanol-water mixture.

7 Claims, No Drawings

METHOD FOR THE SYNTHESIS OF PERMETHRIN

CROSS-REFERENCE TO RELATED APPLICATIONS

This application claims priority to PCT Application No. PCT/IN2017/050377, having a filing date of Sep. 1, 2017, based on Indian Application No. 201641030143, having a filing date of Sep. 2, 2016, the entire contents both of which are hereby incorporated by reference.

FIELD OF TECHNOLOGY

The following describes an improved method for the synthesis of substantially pure pharmaceutical grade Permethrin (1, cis: trans, 25:75) by blending substantially pure Permethrin (6, cis: trans, 2:98) and Permethrin (7, cis: trans, 40:60). The following also relates to a process for the purification of Permethrin to obtain a substantially pure Permethrin (1) or (6) or (7) by recrystallization from methanol-water mixture.

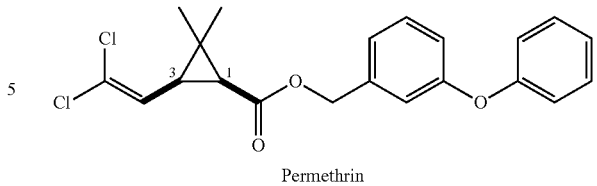

Permethrin

BACKGROUND

Permethrin is chemically known as 3-phenoxybenzyl (1RS,3RS;1RS,3SR)-3-(2,2-dichlorovinyl)-2,2-dimethylcyclopropanecarboxylate.

Permethrin is a photostable synthetic pyrethroid and it is a mixture of four stereoisomers of the configuration ([1R,3S trans], [1R,3R cis], [1S,3R trans], and [1S, 3S cis]). The optical ratio of 1R:1S is 1:1 in a racemic mixture.

1R cis isomer

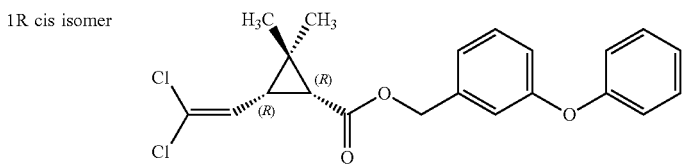

(1R,3R)-3-phenoxybenzyl 3-(2,2-dichlorovinyl)-2,2-dimethylcyclopropanecarboxylate 1S cis isomer

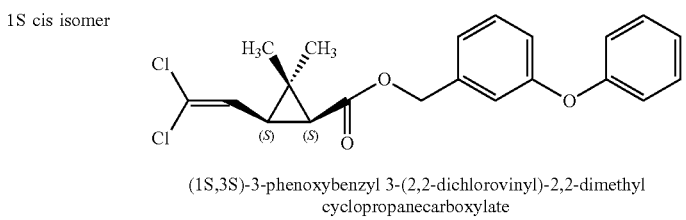

(1S,3S)-3-phenoxybenzyl 3-(2,2-dichlorovinyl)-2,2-dimethyl cyclopropanecarboxylate 1R trans isomer

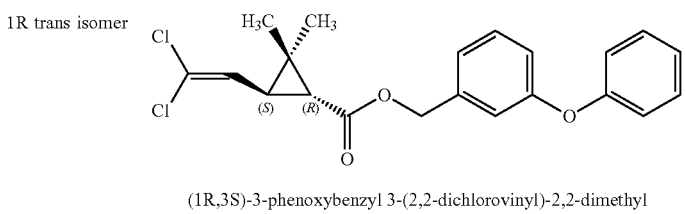

(1R,3S)-3-phenoxybenzyl 3-(2,2-dichlorovinyl)-2,2-dimethyl cyclopropanecarboxylate 1S trans isomer

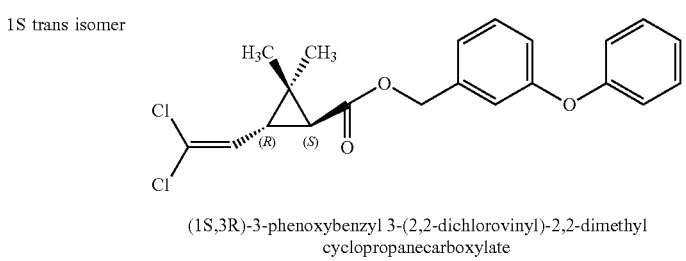

(1S,3R)-3-phenoxybenzyl 3-(2,2-dichlorovinyl)-2,2-dimethyl cyclopropanecarboxylate It is marketed as Elimite in the US as a topical cream for the treatment of scabies caused by *Sarcoptes scabiei*, which is one of the primary indication treated by Permethrin. The cis: trans isomeric ratio in this product is 1:3 i.e. 25:75.

U.S. Pat. No. 4,024,163 describes the esterification of dichloro analogue of chrysanthemic acid, i.e. [1R-trans]-2, 2-dimethyl-3-(2,2-dichlorovinyl) cyclopropane carboxylic acid with 3-phenoxybenzyl alcohol. The desired isomeric ratio of the final product Permethrin (1) is obtained by separating the isomers of the precursor acid chloride and subsequently condensing with (3-phenoxyphenyl) methanol.

U.S. Pat. No. 4,113,968 describes the process for the preparation of Permethrin (1), which involves base hydrolysis of ethyl 2,2-dimethyl-3-(2',2'-dichlorovinyl)-cyclopropane-carboxylate in presence of potassium hydroxide and methanol to obtain acid, which is further treated with thionyl chloride to obtain 2,2-dimethyl-3-(2',2'-dichlorovinyl)-cyclopropane-carboxylic acid chloride. The obtained acid chloride compound (either cis or trans) was coupled with 3-phenoxybenzyl alcohol in the presence of pyridine in benzene as a solvent, to obtain 3-phenoxybenzyl-2',2'-dimethyl-3'-(2",2"-dichlorovinyl)-cyclopropane-carboxylate.

Indian patent IN253251 describes the coupling of 2,2-dimethyl-3-(2',2'-dichlorovinyl)-cyclopropane-carboxylic acid chloride with 3-phenoxybenzyl alcohol without using any solvent at temperature 60-80° C. and continuously expelling hydrochloric acid during the reaction mass into a hydrochloride gas scrubber and washing the crude product to obtain Permethrin (1).

Permethrin produced in the prior art processes suffers from drawbacks like low yield, and lesser purity of the final compound. Further, Permethrin synthesized in the prior art is not purified and carries inherent reaction impurities. To overcome the problems associated with prior art, there is a need to develop an efficient method for commercial scale production of pharmaceutical grade Permethrin, with desired isomeric purity and which is free of reaction impurities.

SUMMARY

An aspect relates to an improved process for the synthesis of substantially pure pharmaceutical grade permethrin designated as Permethrin (1) having desired cis: trans isomeric ratio i. e 25:75.

Another aspect of embodiments of the invention is to provide a process for the purification of Permethrin to obtain a substantially pure Permethrin (1) or (6) or (7) by recrystallization from methanol-water mixture having a purity greater than 99.5% (by GC).

DETAILED DESCRIPTION

The following relates to processes for the preparation of Permethrin (1) in substantially pure form i.e greater than 99.5% with desired cis: trans isomer ratio i.e 25:75.

Accordingly, substantially pure Permethrin 7(cis: trans, 40:60) is blended with required quantity of substantially pure trans Permethrin designated as compound 6 (cis: trans, 2:98) to obtain substantially pure pharmaceutical grade Permethrin (1) with desired isomeric ratio (cis: trans, 25:75) which has GC purity greater than 99.5% and that which is devoid of major reaction impurities (A to H).

The cis: trans isomeric ratio of Permethrin (1) can be controlled by mixing calculated amount of trans Permethrin (6, 2:98) to Permethrin (7, 40:60) by using the following formula:

$$\frac{[(\text{Product } A \text{ weight in } g) \times (\text{Trans ratio of } A)] + [(\text{Product } B \text{ weight in } g) \times (\text{Trans ratio of } B)]}{[(\text{Product } A \text{ weight} + \text{Product } B \text{ weight})]}$$

wherein, Product A is Permethrin (7, 40:60) and Product B is Permethrin (6, 2:98).

Like-wise, Permethrin having varied isomeric content, for example, (cis: trans, 45:55 or 35:65; 43:57; 10:90 or the like) can be blended with required quantities of the substantially pure trans Permethrin (6) to generate substantially pure Permethrin (1). The required quantities of the isomers for blending is calculated by the above formula.

Substantially pure Permethrin (1) can be obtained from any of the precursor isomeric mixture with varied cis: trans isomeric ratio by blending it with a substantially pure trans Permethrin (6) and independently, forms another part of embodiments of the invention. In the above formula, the weight of the Product A is then calculated to be the weight of the Permethrin having varied isomeric ratio, for ex, cis: trans is 45:55; 35:65; 43:57; 10:90 or the like.

Permethrin (6 or 7) in turn is prepared in two reaction steps:

I. First step involves the conversion of 3-phenoxybenzaldehyde (2) to 3-phenoxybenzyl alcohol (3) using suitable reducing agent.

II. Second step involves the coupling of 3-phenoxybenzyl alcohol (3) with 3-(2,2-dichlorovinyl)-2,2-dimethylcyclopropanecarbonyl chloride (5), in suitable solvent at temperature 80-85° C., wherein the cis: trans isomeric ratio of the acid chloride is maintained at 40:60, to yield 3-phenoxybenzyl-3-(2,2-dichlorovinyl)-2,2-dimethyl-cyclopropanecarboxylate (Permethrin whose cis: trans ratio is 40:60, designated as compound 7).

Trans Permethrin (6)(cis: trans, 2:98) is obtained under similar reaction conditions, by maintaining the cis: trans isomeric ratio of the acid chloride (4) at 2:98.

III. Permethrin (7 & 6) obtained in the above step-II is further purified by recrystallizing from a mixture of methanol and water solvent. It is found that in mixture of methanol and water, Permethrin is isolated as a solid and in substantially pure form and forms another part of embodiments of the invention.

In the first step, 3-phenoxybenzaldehyde (2) is converted into (3-phenoxyphenyl) methanol (3) using suitable reducing agent at temperature ranging from 5–25° C., 5-15° C. Reaction completion times range from 1-4 hr, 1-2 hr. Suitable solvent is selected from the group comprising methanol, ethanol, toluene, carbon tetrachloride or mixtures thereof. Suitable reducing agent is selected from the group comprising sodium borohydride, lithium aluminium hydride, diisobutylaluminium hydride, calcium hydride and sodium hydride.

In step-II, (3-phenoxyphenyl) methanol (3) is converted into Permethrin by coupling with 342, 2-dichlorovinyl)-2,2-dimethylcyclopropanecarbonyl chloride (5) at temperature ranging from 80-85° C. Suitable solvent used for the reaction is selected from the group comprising toluene, dichloromethane, ethyl acetate, methyl tertiary butyl ether or mixtures thereof. Permethrin 7 or trans Permethrin 6 is obtained by maintaining the cis: trans isomeric ratio of the acid chloride at 40:60 and 2:98 respectively. Permethrin with varied isomeric ratio may also be generated maintaining the ratio of the acid chloride prior to coupling with (3-phenoxyphenyl) methanol (3). After the completion of the reaction, Permethrin can be purified by recrystallizing from a mixture of methanol and water. The process in general comprises of mixing Permethrin and methanol, heating the mixture to a temperature of about 30-65° C., more between 40-45° C., cooling the temperature to 30-10° C., more between 10-15° C., adding water and bringing the temperature to 0-5° C. The Permethrin thus obtained can be isolated as a solid and in substantially pure form.

The substantially pure Permethrin (7) obtained in step-III is blended with required quantity of substantially pure trans Permethrin (6) to obtain substantially pure Permethrin (1). The GC purity of Permethrin (1) is greater than 99.5% and is devoid of the major reaction impurities (Imp A, B, C, D, E, F, G and H) shown in Table-1. Any unspecified impurity is controlled less than 0.1% (as per the requirement of the European monograph 8.5) and the total impurities are less than 0.5%.

Permethrin (6&7) obtained in the above process or from any other procedures or Permethrin (1) can be purified to obtain a substantially pure compound, by recrystallization from methanol and water mixture as detailed above, and forms a novel part of the present embodiment.

In addition to the above purification process steps in methanol and water mixture, optionally the process further involves, cooling a mixture of methanol and water to 10-15° C., and adding Permethrin crude (1, 7 or 6) to it, cooling the reaction temperature further to 0-5° C. and filtering the solid to obtain Permethrin in substantially pure form.

The following examples further illustrate embodiments of the present invention, but should not be construed in any way as to limit its scope.

TABLE-1

| Impurity | Structure | Chemical Names |
|---|---|---|
| Impurity A | 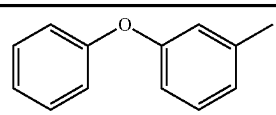 | 1-methyl-3-phenoxybenzene |
| Impurity B | 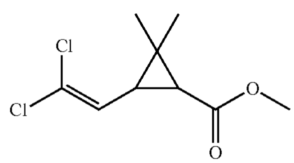 | methyl 3-(2,2-dichlorovinyl)-2,2-dimethylcyclopropanecarboxylate |
| Impurity C | 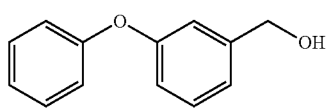 [SMILES: OCc1cccc(Oc2ccccc2)c1] | (3-phenoxyphenyl) methanol |
| Impurity D | 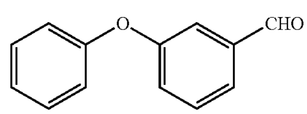 [SMILES: O=Cc1cccc(Oc2ccccc2)c1] | 3-phenoxybenzaldehyde |
| Impurity E | 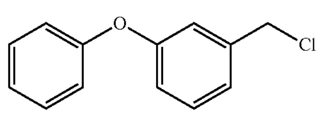 [SMILES: ClCc1cccc(Oc2ccccc2)c1] | 1-(chloromethyl)-3-phenoxybenzene |
| Impurity F | 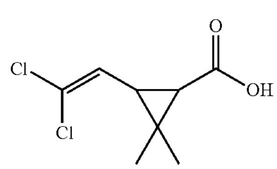 | 3-(2,2-dichlorovinyl)-2,2-dimethylcyclopropanecarboxylic acid |
| Impurity G | 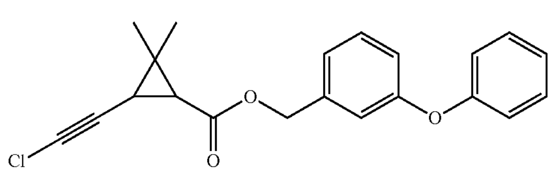 [SMILES: CC1(C)C(C#CCl)C1C(=O)OCc1cccc(Oc2ccccc2)c1] | 3-phenoxybenzyl 3-(chloroethynyl)-2,2-dimethylcyclopropanecarboxylate |
| Impurity H | 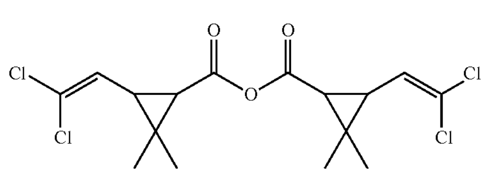 [SMILES: CC1(C)C(C=C(Cl)Cl)C1C(=O)OC(=O)C1C(C=C(Cl)Cl)C1(C)C] | 3-(2,2-dichlorovinyl)-2,2-dimethylcyclopropanecarboxylic anhydride |

Example—1

Preparation of (3-phenoxyphenyl) methanol (3)

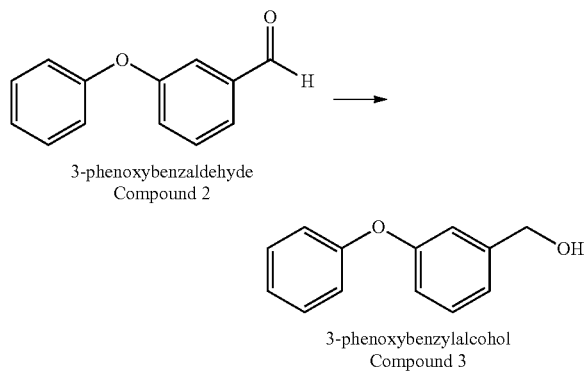

3-phenoxybenzaldehyde
Compound 2

3-phenoxybenzylalcohol
Compound 3

To a clean and dry round bottom flask 500 mL of methanol, 100 g of 3-phenoxybenzaldehyde (2) were charged and stirred for 15-20 minutes at 25-30° C. The mixture was cooled to 5-15° C. and then 19.08 g of sodium borohydride was added lot wise over a period of 2-3 hrs at 5-15° C. The reaction mass was stirred for 1-2 hrs at 10-15° C. After completion of the reaction, the solvent is distilled off completely under vacuum and 200 mL of water was charged, then the reaction mass was stirred for 45-60 minutes at 25-30° C. The product is extracted with 3×100 mL of toluene and the toluene solvent was distilled completely under vacuum. The obtained crude oil was degassed under vacuum at 65-75° C. Yield: 94%.

Example—2

Preparation of 3-phenoxybenzyl 3-(2,2-dichlorovinyl)-2,2-dimethylcyclopropanecarboxylate (Permethrin 6)

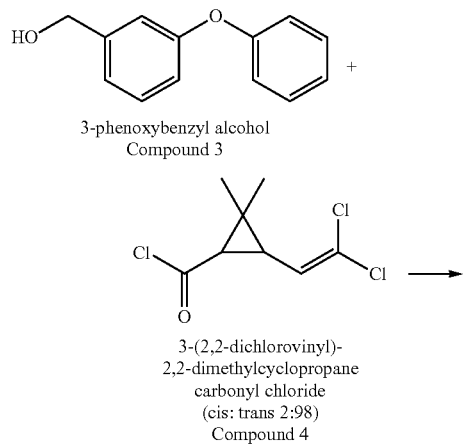

3-phenoxybenzyl alcohol
Compound 3

3-(2,2-dichlorovinyl)-
2,2-dimethylcyclopropane
carbonyl chloride
(cis: trans 2:98)
Compound 4

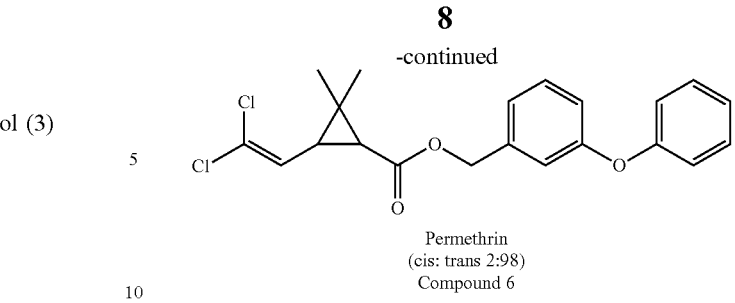

Permethrin
(cis: trans 2:98)
Compound 6

To a clean and dry round bottom flask, 400 mL of toluene and 100 mL of 3-phenoxybenzyl alcohol (3) were charged at 25-30° C. and stirred for 15-20 minutes under nitrogen atmosphere. To this 125 g of 3-(2,2-dichlorovinyl)-2,2-dimethylcyclopropanecarbonyl chloride (4, cis: trans, 2:98) was added drop wise over a period of 60-90 minutes at 25-30° C. The reaction mixture was stirred for 30-60 minutes and raised the temperature slowly to 80-85° C. The reaction temperature is maintained for 3-4 hrs at 80-85° C. After completion of reaction, 200 mL of water was charged and stirred for 10-15 minutes at 40-45° C. The organic layer was separated and washed with water, aqueous sodium chloride solution and followed by water again. The solvent is distilled off completely under vacuum to obtain crude product. To the crude, 720 mL of methanol was added and heated to 40-45° C., the above solution was cooled to 10-15° C. and 1 g of seeding material was optionally added and stirred for 1 hr at 10-15° C. To this, 60 mL of water was added drop wise over a period of 60-90 minutes and maintained for 1 hr. The solution was further cooled to 0-5° C. and maintained for 6-8 hrs, the obtained solid was filtered and washed with chilled methanol. If required, optionally the obtained solid was added to a mixture 680 mL of methanol and 55 mL of water and cooled to 10-15° C. and maintained for 1 hr at 10-15° C., then stirred for 3-4 hrs at 0-5° C. The reaction mass was filtered and the material was suck dried under vacuum. Yield: 70%; Purity by GC: 99.97%.

Example—3

Preparation of 3-phenoxybenzyl 3-(2,2-dichlorovinyl)-2,2-dimethylcyclopropanecarboxylate (Permethrin 7)

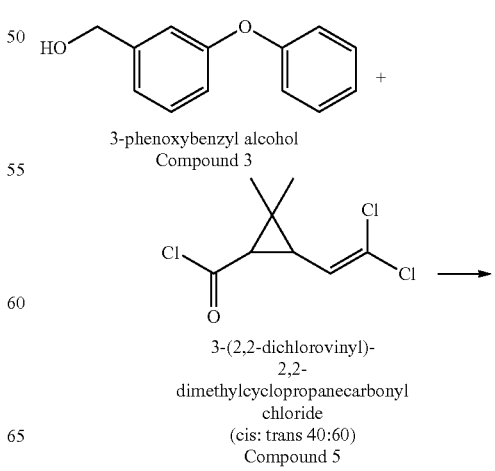

3-phenoxybenzyl alcohol
Compound 3

3-(2,2-dichlorovinyl)-
2,2-dimethylcyclopropanecarbonyl
chloride
(cis: trans 40:60)
Compound 5

-continued

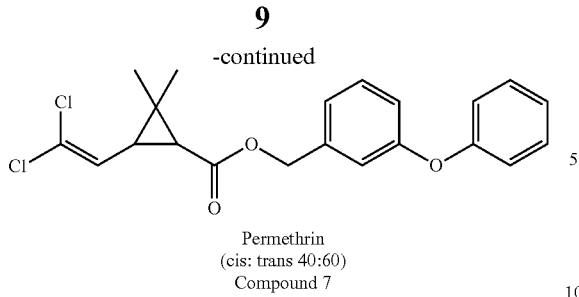

Permethrin
(cis: trans 40:60)
Compound 7

To a clean and dry round bottom flask, 400 mL of toluene and 100 mL of 3-phenoxybenzyl alcohol (3, step-I) were charged at 25-30° C. and stirred the reaction mass for 15-20 minutes under nitrogen atmosphere. To this 125 g of 3-(2, 2-dichlorovinyl)-2,2-dimethylcyclopropanecarbonyl chloride (5, cis: trans 40:60) was added drop wise over a period of 60-90 minutes at 25-30° C. The reaction mass was stirred for 30-60 minutes and slowly raised the temperature to 80-85° C., then maintained the reaction for 3-4 hrs at 80-85° C. After completion of reaction charged 200 mL of water and stirred for 10-15 minutes at 40-45° C., separated organic layer and washed with water, aqueous sodium chloride solution followed by water. Distilled off solvent completely under vacuum. To the crude 720 mL of methanol was added and heated to 40-45° C., the above solution was cooled to 10-15° C., 1 g of seeding material was optionally added and stirred for 1 hr at 10-15° C. To this 60 mL of water was added drop wise over a period of 60-90 minutes and maintained for 1 hr, then this solution was further cooled to 0-5° C. and maintained for 6-8 hrs, the obtained solid was filtered and washed with chilled methanol. If required, optionally the obtained solid was added to a mixture of 700 mL of methanol and 55 mL of water, cooled to 10-15° C., maintained for 1 hr at 10-15° C., then stirred for 3 hrs at 0-5° C. The reaction mass was filtered and the material was suck dried under vacuum.

Yield: 70%; Purity by GC: 99.8%

Example—4

Preparation of 3-phenoxybenzyl 3-(2,2-dichlorovinyl)-2,2-dimethylcyclopropanecarboxylate (Permethrin 1)

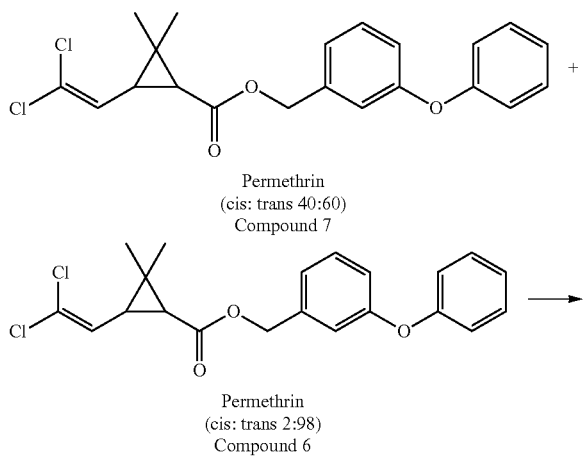

-continued

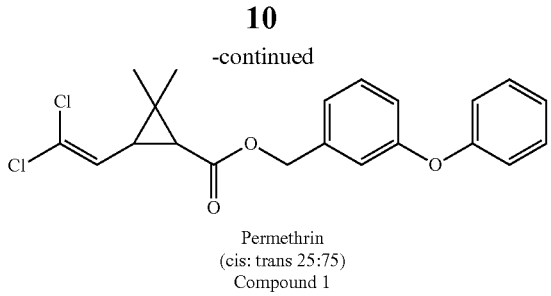

Permethrin
(cis: trans 25:75)
Compound 1

In a clean and dry round bottom flask, 160 g of Permethrin (7) (cis: trans, 40:60) was taken and 100 g of Permethrin (6) (cis: trans, 2:98) was added at 25-30° C. The content of the flask was heated to 45-50° C. to get a liquid mixture, which was stirred for 30 minutes at 45-50° C. to obtain Permethrin with desired Isomeric ratio of (cis: trans, 25:75). The GC purity of the obtained Permethrin (1) is 99.97% with isomer content by chiral HPLC is cis 25.10% and trans 74.90% with (258 g) greater than 95% yield.

Example—5

Preparation of 3-phenoxybenzyl 3-(2,2-dichlorovinyl)-2,2-dimethylcyclopropanecarboxylate (Permethrin 1)

In a clean and dry round bottom flask, 105 g of Permethrin (cis: trans, 47:53) was taken and 100.4 g of permethrin (cis: trans, 2:98) was added at 25-30° C. The content of the flask was heated to 45-50° C. to get a liquid mixture, which was stirred for 30 minutes at 45-50° C. to obtain Permethrin with desired Isomeric ratio of (cis: trans, 25:75). The GC purity of the obtained Permethrin (1) is 99.98% with isomer content by chiral HPLC is cis 25.01% and trans 74.99% with (203 g) greater than 95% yield.

Example—6

Recrystallization of Permethrin (6, 7, & 1)

Permethrin obtained by the instant process or from any other synthetic processes, which has purity less than 99.5% can be purified by crystallizing in methanol and water mixture. This solvent mixture generates greater than 99.5% GC pure Permethrin.

To 100 g of the Permethrin, 720 mL of methanol was added and heated to 40-45° C., the above solution was cooled to 10-15° C., 1 g of seeding material was optionally added and stirred for 1 hr at 10-15° C. To this 60 mL of water was added drop wise over a period of 60-90 minutes and maintained for 1 hr, then this solution was further cooled to 0-5° C. and maintained for 6-8 hrs, the obtained solid was filtered and washed with chilled methanol. If required, optionally, the obtained solid was added to a mixture of 700 mL of methanol and 55 mL of water, cooled to 10-15° C., maintained for 1 hr at 10-15° C., then stirred for 3-4 hrs at 0-5° C. The reaction mass was filtered and the material was suck dried under vacuum. Purity by GC: Permethrin (7)99.82%; Permethrin (6) 99.97%; Permethrin (1) 99.96%

Although the present invention has been disclosed in the form of preferred embodiments and variations thereon, it will be understood that numerous additional modifications and variations could be made thereto without departing from the scope of the invention.

For the sake of clarity, it is to be understood that the use of 'a' or 'an' throughout this application does not exclude a plurality, and 'comprising' does not exclude other steps or elements.

We claim:

1. A process for preparation of substantially pure pharmaceutical grade Permethrin whose purity is greater than 99.5% by blending Permethrin with varied isomeric ratio of cis: trans with trans Permethrin, wherein the weight of the two compounds to be blended is calculated as per the formula:

$$\frac{[(\text{Product } A \text{ weight in g}) \times (\text{Trans ratio of } A)] + [(\text{Product } B \text{ weight in g}) \times (\text{Trans ratio of } B)]}{(\text{Product } A \text{ weight} + \text{Product } B \text{ weight})}$$

wherein, Product A is Permethrin with varied isomeric ratio and Product B is Permethrin.

2. The process of claim 1, wherein Permethrin obtained is devoid of major reaction impurities Imp A, B, C, D, E, F, G and H and total impurities are less than 0.5%.

3. A process for preparation of substantially pure Permethrin with greater than 99.5% purity comprising the steps of:
   I. coupling of 3-phenoxybenzyl alcohol with 3-(2,2-dichlorovinyl)-2,2-dimethylcyclopropanecarbonyl chloride, in a suitable solvent to yield Permethrin
   II. purifying the Permethrin obtained in step I by recrystallizing in methanol and water mixture to obtain a substantially pure Permethrin
   III. blending pure Permethrin of step II of varied isomeric ratio of cis: trans with pure trans Permethrin to obtain substantially pure Permethrin with desired isomeric ratio.

4. The process of claim 3, wherein Permethrin obtained is devoid of major reaction impurities Imp A, B, C, D, E, F, G and H and total impurities are less than 0.5%.

5. The process of claim 3, wherein the coupling reaction of step I is carried out in the presence of organic solvent selected from the group comprising of toluene, dichloromethane, ethyl acetate, methyl tertiary butyl ether or mixtures thereof.

6. The process of claim 3, wherein the coupling reaction of step I is carried out at temperature 80°–85° C.

7. The process of claim 3, wherein the weight of the two compounds to be blended is calculated as per the formula:

$$\frac{[(\text{Product } A \text{ weight in g}) \times (\text{Trans ratio of } A)] + [(\text{Product } B \text{ weight in g}) \times (\text{Trans ratio of } B)]}{[(\text{Product } A \text{ weight} + \text{Product } B \text{ weight})]}$$

wherein, Product A is Permethrin with varied isomeric ratio and Product B is pure trans Permethrin.

* * * * *